United States Patent [19]

Gelbwachs

[11] 4,313,057
[45] Jan. 26, 1982

[54] ULTRASENSITIVE TRACE ELEMENT ANALYZER

[76] Inventor: Jerry A. Gelbwachs, 309 S. Dianthus St., Manhattan Beach, Calif. 90226

[21] Appl. No.: 855,278

[22] Filed: Nov. 28, 1977

[51] Int. Cl.³ .......................... G01J 1/58; G01J 3/30
[52] U.S. Cl. ................................... 250/458; 356/311
[58] Field of Search ........... 250/373, 458, 459, 461 R; 356/85, 98

[56] References Cited

U.S. PATENT DOCUMENTS 3,566,114  2/1971  Brewer ........................... 250/461 B
4,019,060  4/1977  Woodman ......................... 250/458

OTHER PUBLICATIONS

Becker et al., "Fluorescence Determination of Low Formaldehyde Concentrations in Air by Dye Laser Excitation," Applied Optics, vol. 14, No. 2, pp. 310-313, Feb. 1975.

*Primary Examiner*—Alfred E. Smith
*Assistant Examiner*—Janice A. Howell
*Attorney, Agent, or Firm*—Don Finkelstein

[57] ABSTRACT

An arrangement for detecting low concentrations of atoms. A gaseous sample containing the atoms to be detected is provided and the atoms have a plurality of energy levels with photon inducible transitions between a first energy level and a second level and collision inducible transitions between the second energy level and a third energy level. The atoms undergo spontaneous energy emitting transitions from the third energy level to either the first energy level or to a fourth energy level which is collision coupled to the first energy level. A beam of photons which may be generated, for example, by a laser, having photons with a wave length corresponding to the wave length separation between the first energy level and the second level is provided to irradiate the gaseous sample. A buffer gas is provided in order to collide with the atoms at the second energy level thereby inducing transitions to the third energy level. If a fourth level is utilized, collision with the buffer gas also induces transitions from the fourth level back to the first level. A detection means is provided to monitor the wave length emitted by the atoms in the spontaneous transition from the third energy level to either the first energy level or the fourth energy level. The wave length separation between the first energy level and second energy level is different from the wave length separation between the third energy level and either the first or fourth energy level and therefore detection of the energy emitted from the atoms during transitions from the third energy level to the first energy level or fourth level is at a wave length different from the wave length of the photons utilized to induce transitions between the first energy level and second energy level. The intensity of the beam of photons is selected to provide for saturation of the population distribution at the various energy levels in order to maximize the emission rate even in the presence of ambient gases that may tend to quench the characteristic emissions. Thus, detection can take place for the gaseous sample maintained at, for example, one atmosphere pressure. The signal derived from the detection of the wave length emitted by the atoms during transitions from the third energy level to the first energy level or fourth level is a measure of the atomic density in the gaseous sample.

33 Claims, 8 Drawing Figures

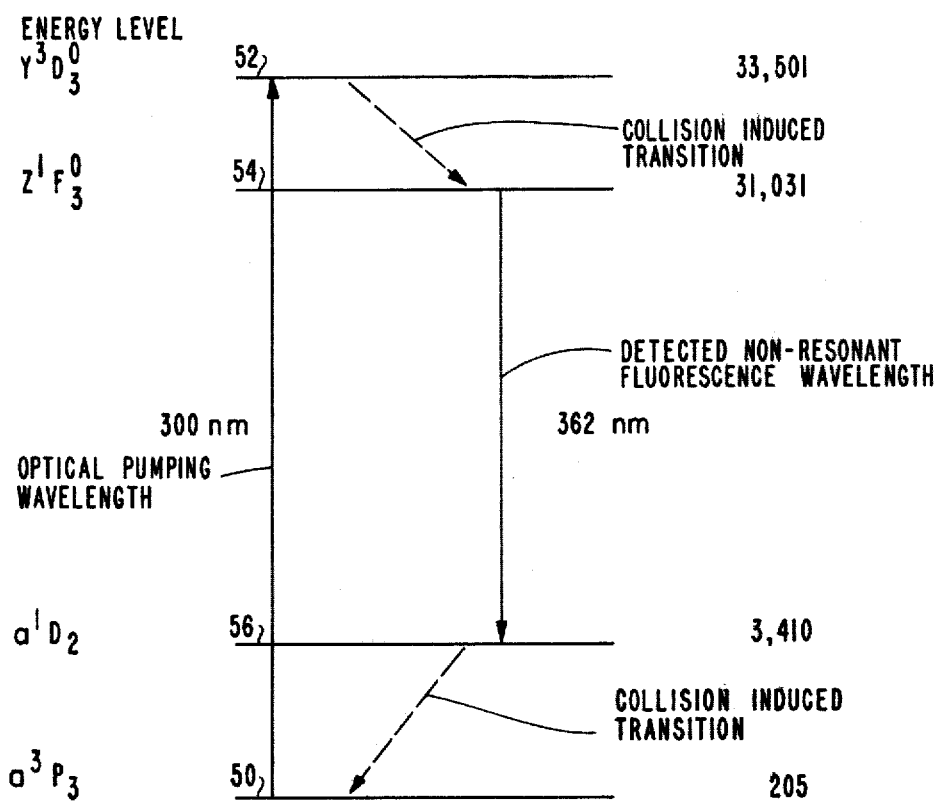
FIG.—3
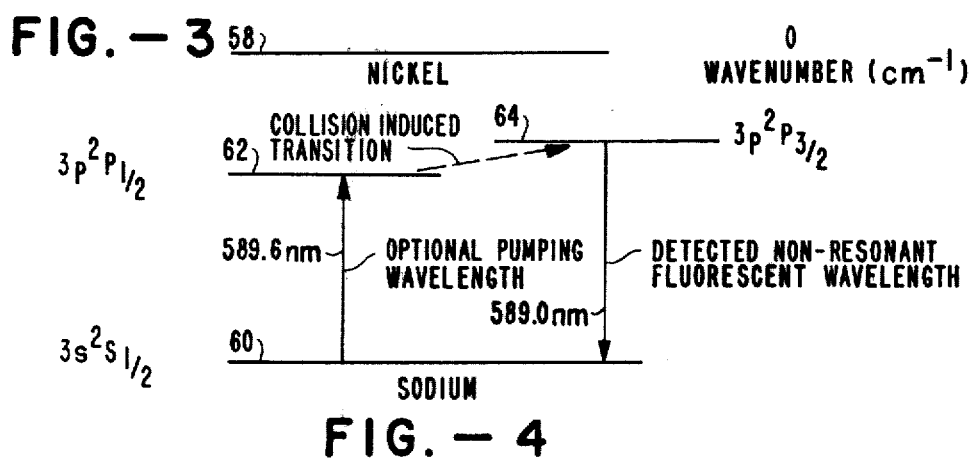
FIG.—4
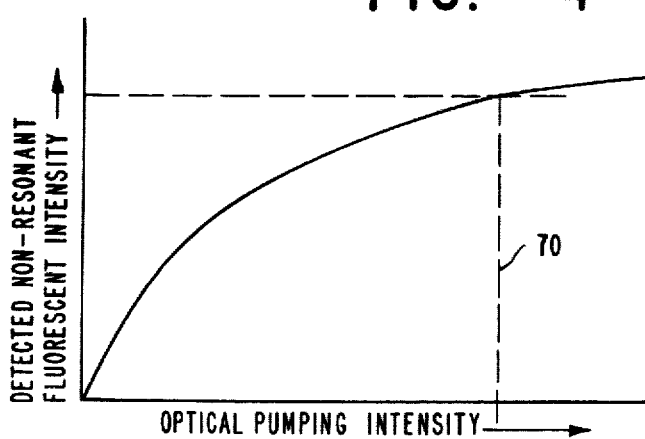
FIG.—5

ULTRASENSITIVE TRACE ELEMENT ANALYZER

BACKGROUND OF THE INVENTION

1. Field of the Invention

This invention relates to the atomic detection art and more particularly to an improved method and apparatus for detecting the presence of very low atomic densities in a gaseous sample.

2. Description of the Prior Art

In many applications such as monitoring trace carcinogens and other environmental pollutants, measuring the constituents of combustion products, measuring biological tracers and chemical vapor tags as well as contaminants in industrial processing it is desirable to be able to detect the presence of comparatively very low densities, for example, on the order of a million down to 1 atom per cubic centimeter. Further, in detecting possible contamination from nuclear waste products the detection of such low concentration of atoms is necessary for establishing procedures to protect both personnel and the environment. Further, to provide ease of detection techniques, it is often desirable that such detection be accomplished in non-enclosed environments and, preferably, at atmospheric pressure.

One prior art method of detecting the presence of such atoms in the environment is atomic absorption spectroscopy. However, the range of detection limits for atomic density utilizing atomic absorption spectroscopy is on the order of $10^8$ to $10^{10}$ atoms per cubic centimeter Another method heretofore utilized for detecting the presence of atoms is atomic fluorescence. In atomic fluorescence techniques, while detection limits have been, in certain specific cases, lowered to approximately $10^2$ atoms per cubic centimeter, they have generally required utilization of comparatively low pressure environments for containing a gaseous sample having the atoms to be detected. It has been found that, for example, at one atmosphere pressure Rayleigh and Mie scattering background emissions and quenching limit the practical use of atomic fluorescence detection techniques to such low pressure conditions.

Detection at pressures of approximately one atmosphere not only provides greater flexibility and more widespread utility in the application of atomic detection but also allows utilization of various atomization sources such as chemical flames, ovens, and electric furnaces to provide the necessary gaseous sample containing the atoms to be detected.

Thus, there is a need for atomic detection and quantitative measuring techniques that not only will allow detection limits down to atomic densities on the order of one atom per cubic centimeter but also for methods that can be used for samples in ambient pressures of one atmosphere.

In other applications such as, for example, quality control techniques in semiconductor fabrication, it is desirable to provide a micro area probe for scanning the surface area of a semiconductor to detect imperfections in, for example, a particular layer of a multi-layered structure. If such imperfections exist, atoms from a sub-surface layer may escape through the imperfection and detection of such escaping atoms down to very low atomic densities can indicate the presence of exceptionally small imperfections.

SUMMARY OF THE INVENTION

Accordingly, it is an object of the present invention to provide an improved atomic detection arrangement.

It is another object of the present invention to provide an improved atomic detection arrangement for detecting comparatively low atomic densities.

It is yet another object of the present invention to provide an improved atomic detection arrangement in which the pressure of the gaseous sample containing the atoms to be detected may be maintained at approximately one atmosphere.

The present invention utilizes certain physical phenomenon and certain characteristics of the atoms to be detected. Therefore, a short description of these phenomenon and characteristics is presented to allow a more complete understanding of the present invention.

The atoms to be detected have certain characteristic energy levels associated with the allowable orbits of their electrons.

Thus, there are a plurality of energy levels associated with the atoms to be detected and the more complex the atomic structure the greater the number of these levels. For example, platinum and uranium have many hundreds of energy levels and specific standardized notations for all levels has not yet been adopted though their values are known.

According to the principals of the present invention in the general case, utilization is made of four of the energy levels of atoms in the gaseous state. In certain specific applications the atomic structure is such that the fourth energy level, as described herein, is the same as the first energy level and, therefore, only three energy levels are thereby utilized.

Optical pumping is a technique for inducing transitions of atoms from a first lower energy level to a second higher energy level by photon absorption. These are termed photon inducible transitions and occur when the wave length of the photon corresponds to the wave length separation between the first and second energy levels. This wave length is often termed the resonance wave length.

Fluorescence is a term utilized to describe the radiative transitions of an atom from a higher to a lower energy level in which photons having a wave length equal to the wave length separation between the higher and lower energy levels are emitted. The intensity of such emitted radiation is a measure of the number of such transitions occurring. The atoms have only a specific lifetime at the higher energy level, and in the absence of other phenomenon spontaneously decay to the lower energy level. In optical pumping applications, the specific fluorescence transition from the higher energy level to which the atom has been optically pumped down to the lower energy level from which it has been pumped is termed resonance fluorescence and photons are emitted by the atoms at the same wave length as the optical pumping photons. Many of the prior art atomic detection techniques have attempted to utilize detection of the resonance fluorescence to identify the presence of particular atoms in a gaseous sample. Therefore, detection was made of radiation at the same wave length as the optical pumping wave length.

Atoms at one energy level may also undergo collision induced transfers to a higher or lower energy level. Such collision induced transfers are caused by collisions of the atoms with other atoms or with molecules and are non-radiative transitions. That is, no photons are emitted by the atoms during the collision induced transitions. When such collision induced transitions occur between the same energy levels associated with fluorescence transitions, it is termed quenching. Quenching reduces the number of atoms available for fluorescence and thus reduces the intensity of the emitted radiation. Therefore, in order to minimize quenching, many prior art resonance fluorescence atomic detection techniques have generally required that the gaseous sample containing the atoms to be detected be maintained at comparatively low pressures in order to minimize the number of other atoms and/or molecules present causing the quenching.

Rayleigh scattering of radiation from ambient molecules and Mie scattering of radiation from non-volatized aerosols or particulate matter are other phenomenon that have limited the applicability of prior art resonance fluorescence atomic detection techniques. That is, the optical pumping radiation may be scattered and thus mask or overpower the resonance fluorescence radiation. In order to avoid such masking effects, the intensity of the optical pumping radiation was often kept to a minimum. However, such low levels of optical pumping intensity reduced the number of atoms available for resonance fluorescence thus decreasing the intensity of the signal to be detected.

Saturation, in optical pumping applications, is defined to mean the condition where the intensity of the optical pumping radiation is at a level where further increases in the optical pumping intensity cause no, or very small, increases in the intensity of the fluorescence radiation. Thus, at saturation, the fluorescence radiation is maximized and, consequently, the fluorescence radiation signal is maximized. Also, at saturation, the population distribution of the atoms at the various energy levels is unique. In the presence of quenching, the saturation condition can still be maintained. This is achieved by increasing the intensity of the optical pumping radiation to a value greater than that necessary to achieve saturation in the abence of the quenching. Therefore, by operating at saturation the fluorescence radiation signal is at maximum to thereby permit detection of very low concentration of the particular atom. However, the intensity levels of the optical pumping radiation and the effects of Rayleigh and/or Mie scattering have heretofore prevented utilization of the saturation condition in prior art resonance fluorescence atomic detection techniques.

The above described phenomenon are uniquely utilized, according to the principles of the present invention, by operating a fluorescence radiation atomic detection arrangement at the saturation condition and detecting a non-resonant fluorescent radiation signal, that is, detecting radiation at a wave length different from the optical pumping wave length. Also, collision induced transitions are intentionally utilized, in conjunction with the optical pumping, to effect the desired energy level transfers. Thus, a maximum detectable signal is obtained even in the presence of quenching and the detectability of the signal is unaffected by Rayleigh or Mie scattering.

According to the principles of the present invention, there is provided a gaseous sample containing the predetermined atoms to be detected. The gaseous sample containing the predetermined atoms may be in a container or in the environment and may be generated by well-known techniques such as an electric furnace, combustion flame, electric arc discharge, ion beam bombardment or microwave discharge.

In the general case, the energy levels of the atom that are utilized are selected so that the following conditions apply.

a. There are photon inducible transitions from a first energy level to a second energy level higher the first energy level.

b. There are collision inducible transitions between the second energy level and a third energy level which may be higher or lower than the second energy level. (This phenomenon is often referred to as "collision coupled energy levels.")

c. There are fluorescent radiative transitions between the third energy level and a fourth energy level.

d. There are collision inducible transitions between the fourth energy level and the first energy level, and the fourth energy level may be higher or lower than the first energy level.

e. The wave length associated with the energy separation between the first and the second energy levels is different from the wave length associated with the energy separation between the third and the fourth energy levels.

In a special case, depending upon the atom, the fourth energy level is the same level as the third energy level.

A beam of photons having a wave length corresponding to the energy separation between the first and second energy levels of the atom to be detected is utilized for optically pumping the atoms from the first to the second energy level. The photon beam may be conveniently generated by a laser which may be either continuous wave or pulsed. The laser is operated at an intensity level providing saturation of the energy levels of the atom to be detected.

A buffer gas is also provided in regions containing the gaseous atoms to be detected. The buffer gas provides the necessary collision induced transitions of the atoms as utilized in the practice of the invention herein. That is, the buffer gas provides the collision induced transitions from the second to the third energy levels of the atom and, if required, between the fourth and the first energy levels. Even though the buffer gas also induces quenching, as described above, according to the principles of the present invention, by operation of the laser at a saturation intensity, the effects of such quenching are eliminated and detection of the atoms at even very low atomic densities in the gaseous samples may be accomplished.

After the atoms have undergone the collision induced transitions from the second to the third energy level, they undergo the non-resonant radiative transitions from the third energy level to the fourth energy level. During this transition they emit radiation at a wave length different from the optical pumping wave length. Since the optical pumping is maintained at a saturation level, the intensity of the non-resonant radition is maximized.

A detection means is provided to detect the non-resonant radiation and generates a signal having a magnitude proportional to the intensity thereof. The intensity of the non-resonant radiation emitted in the transition from the third to the fourth energy level is a measure of the concentration of the atoms to be detected, or the density thereof, in the gaseous sample.

The atoms then undergo collision induced transitions due to the presence of the buffer gas from the fourth energy level to the first energy level, and the process is repeated as long as the optical pumping is continued.

BRIEF DESCRIPTION OF THE DRAWINGS

The above and other embodiments of the present invention may be more fully understood from the following detailed description taken together with the accompanying drawings wherein similar reference characters refer to similar elements throughout and in which:

FIGS. 1, 2, 3 and 4 are graphical representations of physical characteristics of atoms applicable to the present invention;

FIG. 5 is a graphic representation of other characteristics applicable to the practice of the present invention;

The specific structural details described and illustrated herein are utilized for illustrative purposes only to explain the principles of the present invention and are not to be construed in a limiting sense. The invention herein is limited only by the appended claims.

DESCRIPTION OF THE PREFERRED EMBODIMENTS

Figure 1:
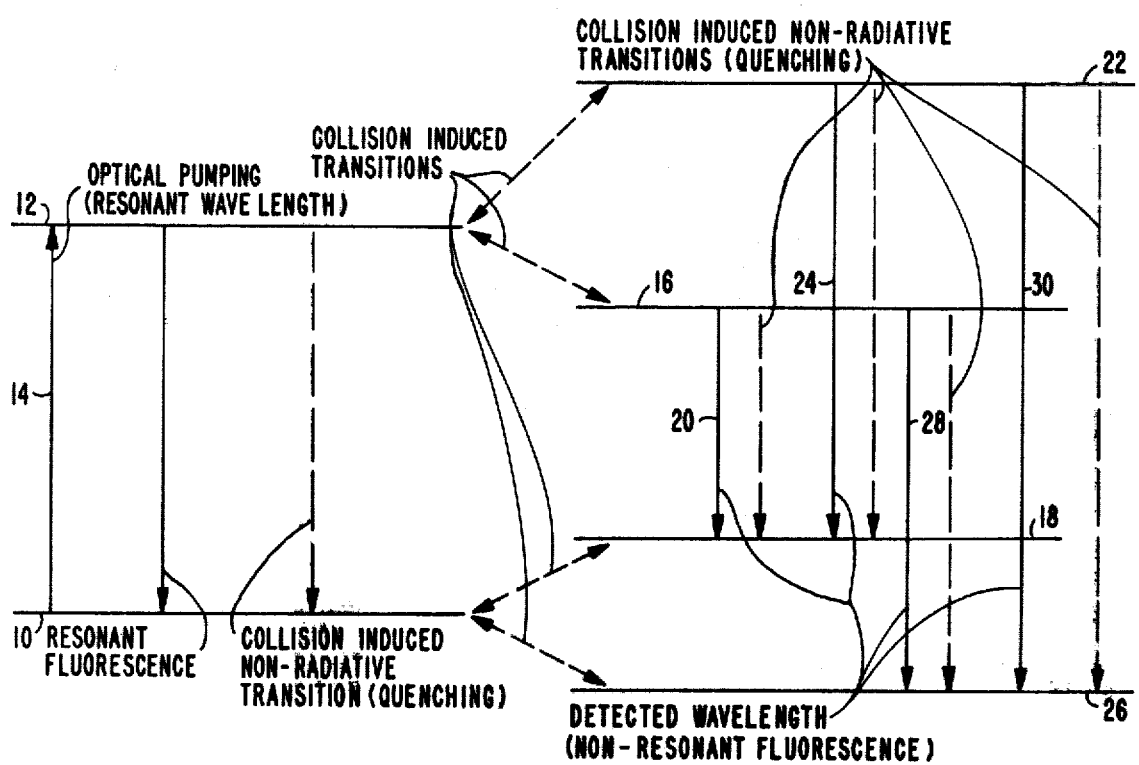

FIGS. 1, 2, 3, 4 and 5 illustrate the various physical phenomenon and characteristics described above. Referring to FIG. 1, there is illustrated a graphical representation of an atomic energy level diagram illustrating the various transitions described above and as associated with the present invention. Atoms at a first energy level indicated at 10 are subjected to an optical pumping radiation comprising a photon beam having energies at the resonant wave length corresponding to the energy separation between the first energy level 10 and the second energy level 12. The optical pumping resonant wave length is indicated by the arrow 14. The atoms at the first energy level can absorb energy from the photons in the optical pumping radiation and this causes transitions of at least some of the atoms to the second energy level 12. Thus, according to the principles of the present invention, the second energy level 12 is higher than the first energy level 10. The atoms are in the presence of a buffer gas and the buffer gas provides collision induced transitions from the second energy level 12 to a third energy level 16. The collision induced transitions between the second energy level 12 and third energy level 16 are non-radiative transitions. From the third energy level 16 the atoms undergo fluorescence to the fourth energy level 18. The energy level separation between the third energy level 16 and fourth energy level 18 is different from the energy level separation between the first energy level 10 and second energy level 12. The non-resonant fluorescence in the transition of the atoms from the third energy level 16 to the fourth energy level 18 is the detected wave length 20 that is detected according to the principles of the present invention.

From the fourth energy level 18 the atoms undergo collision induced transitions due to collisions with the buffer gas back to the first energy level 10.

According to the principles of the present invention the third energy level 16 need not be lower than the second energy level 12. As shown on FIG. 1 the third energy level 16 may, for example, be higher than the second energy level 12 as indicated at 22. In such an energy level structure the detected wave length may comprise the non-resonant fluorescence between the third energy level 22 and the fourth energy level 18 as indicated at 24. The wave length of the non-resonant fluorescence 24 is different from the optical pumping resonant wave length corresponding to the transitions between first energy level 10 and second energy level 12. The buffer gas provides a collision induced transition from the second energy level 12 to the third energy level 22.

Similarly, the fourth energy level may not necessarily be higher than the first energy level. For example, the fourth energy level may be lower than the first energy level 10 as indicated at 26. In such embodiments the detected wave length of non-resonant fluorescence may be as indicated at 28 between the third energy level 16 and fourth energy level 26 or the non-resonant fluorescence between third energy level 22 and fourth energy level 26 as indicated at 30. Collisions with the buffer gas provides the transitions from the fourth energy level 26 to the first energy level 10.

It will be appreciated, of course, that, depending upon the atomic spectra, the third energy level may be at the same energy at the second energy level but, in such applications, the fourth energy level is not the same energy level as the first energy level. Thus, the detected wave length would be a non-resonant fluorescence and the buffer gas would provide the collision induced transitions from the fourth energy level to the first energy level.

In yet other embodiments, depending upon the atomic spectra, the fourth energy level may be the same as the first energy level but, in such embodiments, the third energy level is different from the second energy level with the buffer gas providing the collision induced transitions between the second and third energy levels. In all applications of the present invention, however, the detected wave length is different from the optical pumping resonant wave length.

It will be appreciated that atoms at the second energy 12 also undergo fluorescence in transitions back to the first energy level 10 and this is termed the resonant fluorescence since it is at the same wave length as the optical pumping resonant wave length 14. Similarly, collisions with the buffer gas may induce transitions between the second energy level 12 and first energy level 10 which are non-radiative as well as non-radiative transitions between third energy level 16 or 22 and fourth energy level 18 or 26. These collision induced transitions are also non-radiative. Such collision induced transitions are termed quenching since they occur between the particular energy levels associated here with the optical pumping or with the detection. According to the principles of the present invention, as below in connection with FIG. 5, the effects of resonant fluorescence and/or quenching which would tend to decrease the detectable signal strength at the detected wave length of non-resonant fluorescence are minimized by operating the optical pumping resonant wave length 14 at saturation intensities in order to maximize the population distribution throughout the various energy levels pertinent to the practice of the present invention. Similarly, by providing a buffer gas at pressures, for example, of one atmosphere collision induced transitions necessary for the practice of the present invention such as those between second energy level 12 third energy levels 16 or 22 and between fourth energy levels 18 or 26 and first energy level 10 are intentionally utilized in the practice of the present invention.

The collision induced transitions between second energy level 12 and third energy level 16 or 22, and between fourth energy levels 18 or 26 and first energy level 10 are shown as double ended arrows since such non-radiative collision induced transitions may occur in both directions.

Figure 2:
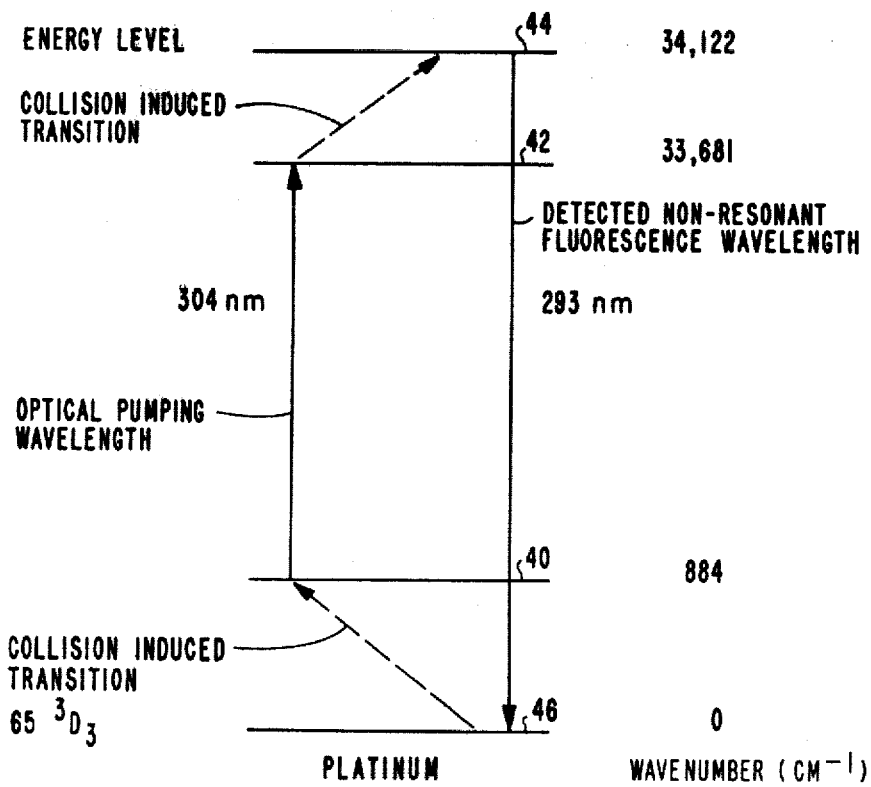

Referring now to FIG. 2 there is illustrated an energy level diagram for platinum according to the principles of the present invention. The first energy level 40, the second energy level 42 and third energy level 44 do not have standardized notation for designating such energy levels but the fourth energy level 46 does have such a standarized notation and is 6S $^3D_3$ level. However, wave numbers for each of these energy levels have been determined and are as shown on FIG. 2. When atoms at the first energy level 40 are subjected to an optical pumping wave length of 304 nm transitions are induced to the second energy level 42 by photon absorption.

The atoms of platinum are in the presence of a buffer gas and undergo collision induced transitions from the second energy level 42 to the third energy level 44. The atoms then undergo fluorescence from the third energy level 44 to the fourth energy level 46 and this detected non-resonance fluorescence wave length is 293 nm. Collisions with the buffer gas then provide the non-radiative transitions between the fourth energy level 46 and first energy level 40. As shown on FIG. 2, the fourth energy level 46 is the ground energy level for platinum. Thus, according to the principles of the present invention, depending upon the atomic spectra the first energy level does not necessarily correspond to the ground energy level of the particular atom to be detected. Thus, for the platinum atom as shown on FIG. 2, the energy level transitions according to the principle of the present invention correspond to energy level transitions 10-12-22-26 as illustrated on FIG. 1 and, of course, the detected non-resonant fluorescent wave length of 293 nm is different from the optical pumping resonant wave length 304 nm.

Referring now to FIG. 3 there is illustrated an energy level diagram for nickel. The first energy level indicated at 50 corresponds to the $a^3P_3$ level. An optical pumping resonant wave length of 300 nm induces transitions from the first energy level 50 to the second energy level 52 which is the $Y^3D_3^0$ energy level. A buffer gas provided in the presence of the nickel atoms provides the collision induced transitions from the second energy level 52 to the third energy level 54 which is the $Z^1F_3^0$ energy level. From the third energy level 54 the atoms undergo a non-resonant fluorescent transition to the fourth energy level 56 at a wave length of 362 nm and this is the detected wave length according to the principles of the present invention. The presence of the buffer gas provides the collision induced transitions from the fourth energy level 56 to the first energy level 50. As can be seen from FIG. 3, the energy level transitions associated with nickel correspond to energy level transitions 10-22-16-18 illustrated on FIG. 1. Further, as shown on FIG. 3, the ground energy level 58 of nickel as indicated by wave number 0 is not one of the energy levels utilized in the detection of nickel atoms according to the principles of the present invention for the particular energy transitions shown on FIG. 3. Thus, for nickel, the optical pumping wave length of 300 nm is different from detected non-resonant wave length of 362 nm.

FIG. 4 illustrates an energy level diagram for sodium and the first energy level 60 corresponds to 3s $^3S_{\frac{1}{2}}$ energy level and optical pumping resonant wave length of 589.6 nm was utilized to cause transitions to the second energy level 62 which is the 3p $^2P_{\frac{1}{2}}$ energy level. The presence of a buffer gas causes collision induced transitions from the second energy level 62 to a third energy level 64 which is the 3p $^2P_{3/2}$ energy level and the atoms of sodium undergo a non-resonant fluorescence transition from the third energy level 64 to the first energy level 60 at a wave length of 589.0 nm. Thus, for the sodium atom the fourth energy level is the same energy level as the first energy level. However, the detected wave length of 589.0 nm is different from the resonant optical pumping wave length of 589.6 nm.

In FIGS. 2, 3 and 4 the arrows indicating resonant fluorescence and quenching have been omitted for clarity. However, such phenomenon do occur as described above in connection with FIG. 1.

The intensity of the detected non-resonant fluorescent wave length is a measure of the number of atoms undergoing the particular transition and thus is a measure of the concentration of the atoms. In order to maximize the intensity of the signal the optical pumping beam is operated at a saturation intensity level. At saturation the population distribution among the various energy levels associated with the practice of the present invention is maximized and even comparatively large changes in the intensity of the optical pumping provides very small changes in the intensity of the detected non-resonant fluorescence. This phenomenon is graphically illustrated in FIG. 5 and shows the relationship of the optical pumping resonant wave length intensity to the intensity of the detected non-resonance fluorescence. As can be seen, at the saturation levels indicated at 70 even comparatively large increases in the optical pumping intensity does not provide any substantial increase in the intensity of the detected non-resonance fluorescence. It will be appreciated, of course, that the intensity level necessary to achieve saturation depends upon many factors associated with the practice of the present invention. For example, the greater the pressure of the buffer gas in the presence of the atoms to be detected the greater will be the amount of quenching provided by the collision induced transitions of the atoms with the buffer gas. However, by increasing the intensity of the optical pumping saturation can be achieved even at, for example, one atmosphere pressure. However, it will be appreciated, that the principles of the present invention may also be utilized where the atoms are at pressures less than or greater than one atmosphere in the presence of the buffer gas. Similarly, the effects of resonant fluorescence are also minimized by operation at saturation. Thus, operation at saturation provides an intensity level of the optical pumping to maximize the intensity of the detected non-resonant fluorescence. Since the maximum number of atoms are then participating in the non-resonant fluorescent transitions, the detected intensity at saturation can be indicated in absolute values of the number of atoms per cubic centimeter.

Table I lists the parameters associated with atomic detection according to the principles of the present invention for various atoms. As shown on Table I for certain atoms such as platinum and uranium standardized energy level notation has not yet been adopted. However, the energy levels appropriate for practice of the present invention and the separations therebetween are known. Additionally, for certain atoms there is no listing for an energy level shown in the column headed Fourth Energy Level since detection of such atoms is achieved according to the principles of the present invention by utilizing only three energy levels such as that shown for sodium in FIG. 4.

corresponding to the particular non-resonant fluorescence wave length that is to be detected as emitted from the atoms 80. The buffer gas 82 provides the collison induced transitions, as described above, such as, for example, inducing the transitions of the atoms 80 from the second energy level thereof to which they have been raised by absorption of energy from the photon

TABLE I

| Atom | First Energy Level | Second Energy Level | Third Energy Level | Fourth Energy Level | Laser | Optical Pumping Frequency nm | Detection Frequency nm |
|---|---|---|---|---|---|---|---|
| Ni | a $^3P_3$ | y $^3D_3^0$ | z $^1F_3^0$ | a $^1D_2$ | Frequency-doubled chodamine-6G dye | 300.3 | 361.9 |
| Se | $4_p{}^4{}^3P_2$ | 5s $^5S_2^0$ | 5s $^3S_1^0$ | | Argon floride excimer | 207.5 | 196.0 |
| K | 4s $^2S$ | 4p $^2P_{1/2}^0$ | 4p $^2P_{3/2}^0$ | | DOTC-dye | 770.1 | 766.7 |
| B | 2p $^2P_{3/2}$ | 2p$^2$ $^2D$ | 3s $^2S$ | 2p $^2P_{1/2}$ | Argon-Fluoride excimer | 209.0 | 249.8 |
| Al | 3p$^2$ $^3P_2$ | | 4d $^2D_{5/2}$ | | Coumarin-6 Dye | 266.0 | 257.5 |
| Pt | * | * | * | 6s $^3D_3$ | Frequency-doubled rhodamine-6G Dye | 304.3 | 293.0 |
| Si | $3_p{}^2$ $^3P_2$ | 4s $^3P_2^0$ | 4s $^1P^0$ | 3p$^2$ $^1D_2$ | Frequency-doubled Coumarin-102 Dye | 251.4 | 288.2 |
| Sc | a $^2D_{1/2}$ | y $^2D_{3/2}^0$ | y $^2F_{5/2}^0$ | | PBBO | 402.0 | 390.7 |
| Ti | a $^3F_2$ | v $^3F_2^0$ | z $^1P_1^0$ | a $^1D_2$ | Frequency-doubled Chodamine-6G dye | 294.2 | 378.6 |
| Cr | a $^7S_3$ | y $^7P_2^0$ | z $^5P_3^0$ | a $^5S_2$ | PBD dye | 360.5 | 520.8 |
| Sn | 5p$^2$ $^3P_0$ | 6s $^1P_1^0$ | 6s $^3P_2^0$ | 5p$^2$ $^1D_2$ | Frequency-doubled C485-Dye | 254.7 | 333.1 |
| As | 4p$^3$ $^4S_{3/2}^0$ | 5s $^4P_{3/2}$ | 5s $^4P_{1/2}$ | 4p$^3$ $^2D^0$ | Argon fluoride excimer | 193.7 | 249.3 |
| Sb | Sp$^3$ $^4S_{3/2}^D$ | 6s $^4P_{5/2}$ | 6s $^2P_{3/2}$ | 5p$^3$ $^2P_{3/2}^0$ | Argon fluoride excimer | 206.8 | 323.2 |
| Rb | 5s $^2S_{1/2}$ | 5p $^2P_{1/2}^0$ | 5p $^2P_{3/2}^0$ | | DOTC-dye | 794.8 | 780.0 |
| Cs | 6s $^2S_{1/2}$ | 7p $^2P_{1/2}^0$ | 6d $^2P_{3/2}^0$ | 6p $^2P_{1/2}^0$ | Coumarin-2 Dye | 455.5 | 876.1 |
| Pb | 6p$^2$ $^3P_0$ | 7s $^3P_1^0$ | 7s $^3P_0^0$ | 6p$^2$ $^3P_1$ | Frequency-doubled Rhodamine-6G dye | 283.3 | 368.3 |
| U | * | * | * | * | Xenon fluoride excimer | 353.4 | 399.9 |

*Standardized energy level notation not yet adopted

Figure 6:
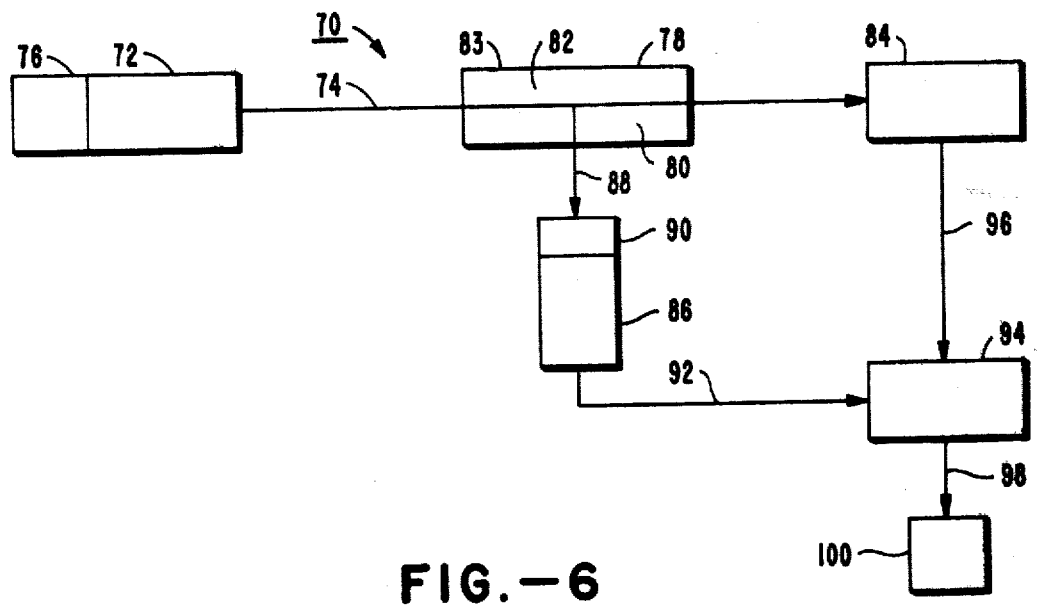
FIG. 6 is a block diagram of an apparatus useful in the practice of the present invention.

Referring now to FIG. 6 there is illustrated one embodiment generally designated 70, in block diagram form, of an apparatus useful in the practice of the present invention. As shown in FIG. 6 there is provided a laser 72 for generating a photon beam 74 having a preselected intensity and contains photons having a predetermined wave length. The laser 72 is powered by a power supply 76. The laser 72 may be a continuous wave laser or a pulsed laser depending upon the particular application.

An atomizer 78 is utilized to provide a gaseous sample containing the predetermined atoms 80 to be detected. It will be appreciated that, according to the principles of the present invention, any desired type atomizer may be utilized as the atomizer 78. That is, the atomizer 78 may be an electric furnace, a combustion flame such as an air acetylene mixture, an electric arc discharge, an ion beam bombardment, a microwave discharge or the like. The particular method of atomization utilized herein does not, per se, form the present invention and the present invention uniquely allows utilization of many types of atomizers which have not heretofore been utilized in prior art atomic detection techniques.

The beam of photons 74 is at a wave length corresponding to the resonant wave length for the atoms 80 to be detected and provides the optical pumping for inducing the transitions of the atoms 80 from a first energy level to a second energy level as discussed above in connection with FIGS. 1, 2, 3 and 4. The intensity of the photon beam 74, which is the optical pumping beam, is selected, in preferred embodiments of the present invention to provide a saturation intensity as discussed above in connection with FIG. 5. The photon beam 74 is also, in preferred embodiments of the present invention, substantially free of photons at a wave length beam 74 to a third energy level. If desired, a power meter 84 may be utilized to detect the intensity of the photon beam 74 after it has irradiated the gaseous sample having the atoms 80. The gaseous sample having the atoms 80 and buffer gas 82 may be in the open air at atmospheric pressure, in which case the ambient air comprises the buffer gas 82, or may be contained within a container 83 having at least portions of its walls transparent to the resonant wave length of the photon beam 74 and the preselected non-resonant fluorescence wave length.

A detection means 86 is provided to detect the non-resonant fluorescence radiation emitted by the atoms 80 in the transition from the third energy level thereof to the fourth energy level as indicated by the arrow 88. The detection means 86 may also incorporate a filter means 90 which transmits only the non-resonant fluorescent wave length 83. Where the atomic spectra of the atoms to be detected 80 is such that four energy levels are utilized, the buffer gas 82 provides the collision induced transitions of the atoms 80 from the fourth energy level to the first energy level thereof.

The detector means 86 may be a photon detector or similar structure and generates a first information signal 92 having a magnitude proportional to the intensity of the non-resonant fluorescent wave length 88 and the first information signal is transmitted to a signal processing means 94. The signal processing means 94 is also connected to the power meter 84 for receiving a second information signal 96 generated by the power meter 84 and the second information signal 96 has a magnitude proportional to the detected intensity of the photon beam 74 after irradiation of the gaseous sample 80. The signal processing means 94 ratios the first information signal 92 and second information signal 96 to provide an output signal 98 having a magnitude proportional to this ratio and the output signal 98 may be displayed in any desired type of display such as a meter, digital read out or the like as indicated at 100. With the embodiment 70 operating at a saturation intensity of the photon beam 74 the output signal 98 from the signal processor 94 is proportional to the concentration of the atoms 80 in the volume subjected to the photon beam 74.

It will be appreciated, of course, that the filter 90 may be any desired type of filter such as a spectrometer, prism, narrow band pass interference filter, gas filter, or the like.

In preferred embodiments of the present invention the detection is made with the gaseous sample having the atoms 80 at one atmosphere pressure to allow convenient utilization in non-laboratory environments such as on-site testing and evaluation. However, it will be appreciated, lower or higher pressures may also be utilized. That is, the present invention may be conveniently operated with the atoms 80 to be detected at, for example, one Milli Torr to one thousand atmospheres. Where particular pressures are selected to be other than atmospheric, containers must be provided for containing the atoms 80 to be detected. Similarly, if the atoms to be detected are reactive with air, such as sodium, it may be desirable to provide a container as part of the atomizer, evacuating the air therefrom and refilling with a buffer gas comprising a noble gas such as argon or helium. Because the emission rate of non-resistant fluorescence is independent of the quenching effect of the buffer gas, the particular pressure selected may be chosen on considerations other than the quenching effect of the buffer gas.

If fluorescent molecules are present in regions containing the atoms 80 to be detected, the effect thereof can be reduced and/or eliminated. Since the molecular absorption cross-section is much less than that of an atomic resonant transition, such molecular transitions will not saturate at the intensity levels that saturate the atomic transitions. Therefore, modulation of the intensity of the photon beam 74 by, for example, modulating the power supply 76, an AC signal is produced wherein the variations in intensity will be primarily dictated by the molecules present. By eliminating the AC component the virtually unaffected detected energy as indicated by the detected non-resonant fluorescence 88 is determined. The signal processor 94 may incorporate conventional techniques for eliminating the AC component from the first information signal 92 and the second information signal 96.

Figure 7:
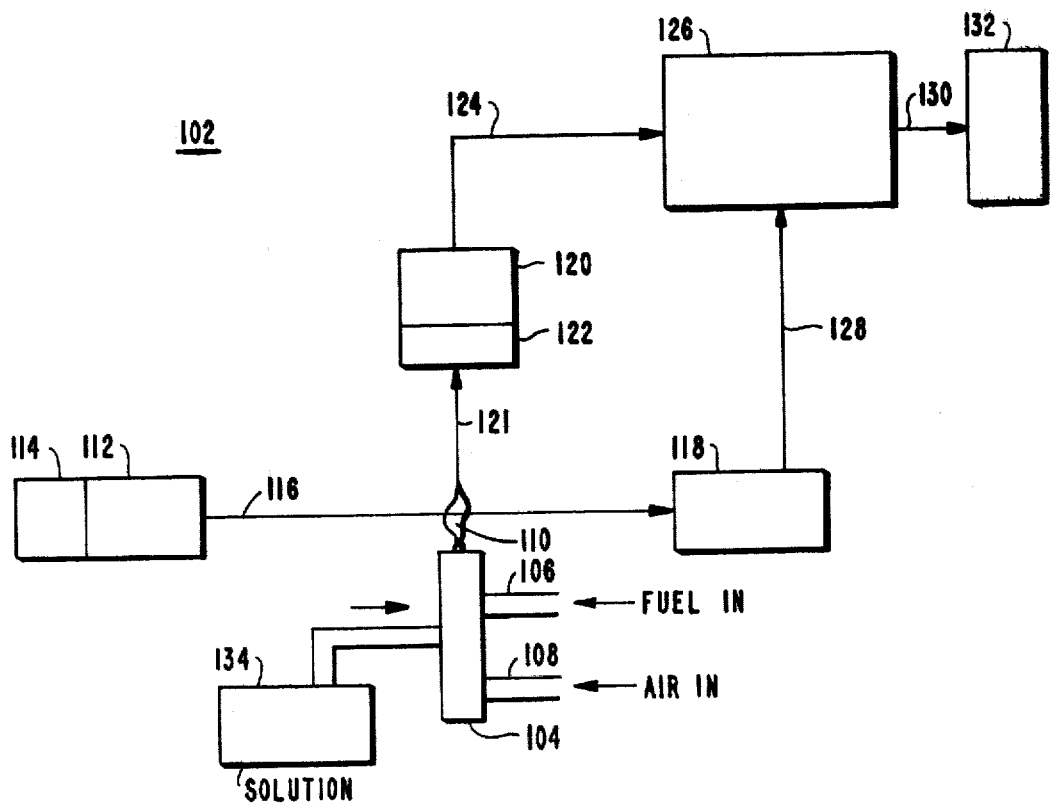
FIG. 7 illustrates another apparatus useful in the practice of the present invention.

FIG. 7 illustrates another embodiment, generally designated 102 of the present invention for detecting the concentrations of predetermined atoms. As shown in FIG. 7 an atomizer 104 is provided which, in the embodiment 102 may be flame atomizer having a fuel supply 106 and ambient air supply 108. The embodiment 102, therefore, may be utilized to detect the presence of predetermined atoms in the ambient air. The atomizer 104 has a combustion flame 110 which provides the desired atomization. Thus, the atomizer 104 operates at the ambient pressure and detection of the atoms in the ambient air is made at the ambient pressure.

A laser 112 powered by a power supply 114, which may be similar to the laser 72 and power supply 76 described above, generates a photon beam 116 having an intensity corresponding to a saturation intensity for the particular atoms that are to be detected and contains photons at a wave length corresponding to the resonant transition of the atoms to be detected. The photon beam 116 is also, preferably, substantially free of photons at a wave length corresponding to the resonant fluorescent wave length that is to be detected. A power meter 118 which may be similar to the power meter 84 described above receives the photon beam 116 after it has traversed the area containing the flame 110 wherein the atomization is provided. In the embodiment 102 the gaseous products of combustion provide the buffer gas in the regions containing the atoms to be detected.

A detector 120 is provided and may be similar to the detector 86 described above and have a filter 122 similar to the filter 90 described above for detecting the non-resonant fluorescence from the atoms to be detected. The detector 120 generates a first information signal 124 having a magnitude proportional to the intensity of the detected non-resonant fluorescence 121 and the first information signal 124 is transmitted to a signal processor 126 which may be similar to the signal processor 94 described above. The power meter 118 generates a second information signal 128 which is also transmitted to the signal processor 126 which, as described above, generates an output signal 130 having a magnitude proportional to the ratio between the first information signal 124 and second information signal 128 which is provided to a display 132 which may be similar to the display means 100 described above.

Operation of the embodiment 102 may be the same as operation of the embodiment 70 described above and the first information signal 124 is, therefore, proportional to the number of atoms to be detected present in the ambient air.

In some applications it may be desirable to determine the concentration of atoms in a liquid medium such as water or the like. In such an embodiment a solution containing the atoms to be detected may be connected to the atomizer 104 as indicated at 134 and the solution is atomized by the atomizer 104 for detection of the predetermined atoms contained therein.

Figure 8:
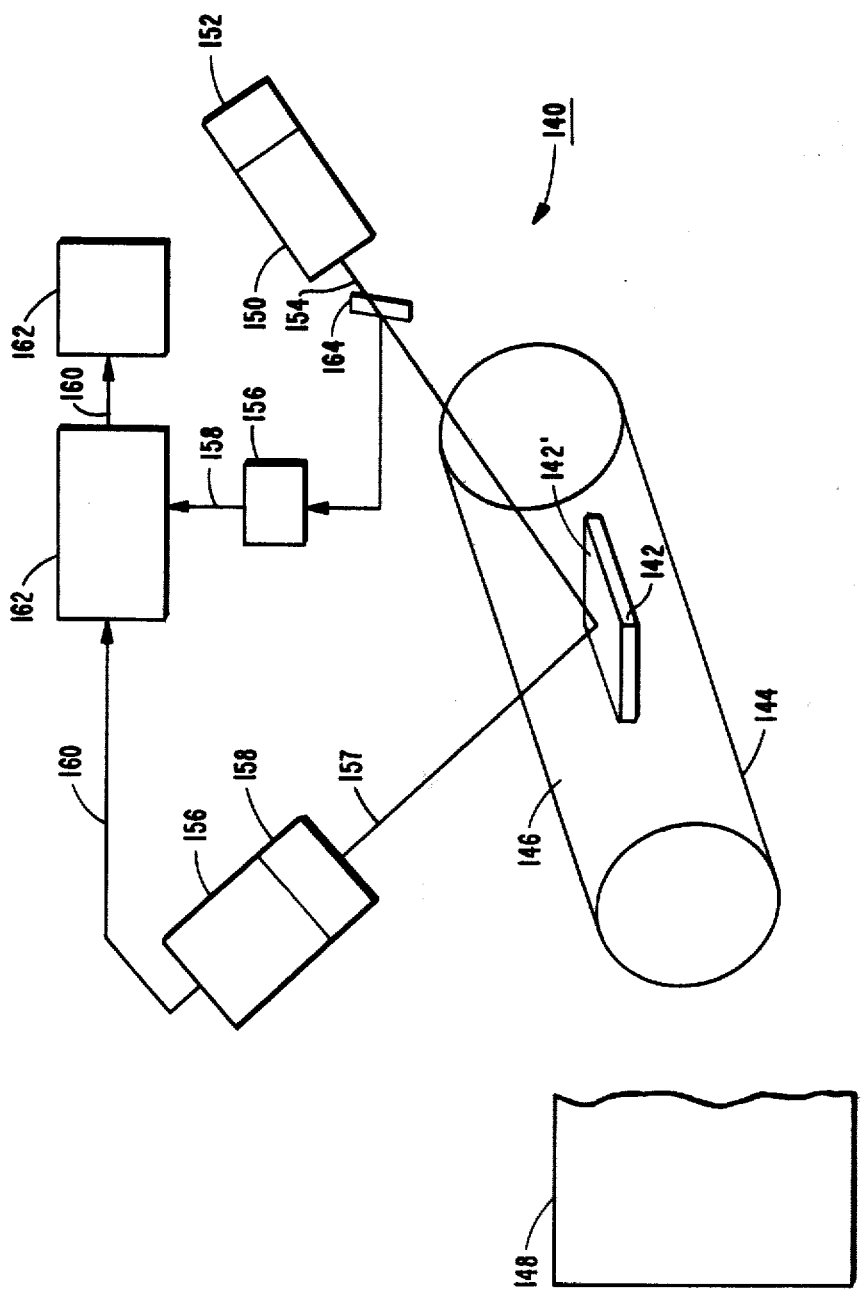
FIG. 8 illustrates another apparatus useful in the practice of the present invention.

In yet other applications of the present invention it may be desirable to detect imperfections in various items over an extended surface area thereof, for example, a multi-layered transistor or the like. It may be desirable to detect whether or not one of the layers has completely covered the sub-surface layer. FIG. 8 illustrates an embodiment generally designated 140 for application of the principles of the present invention to such a quality control inspection technique. As shown, in the embodiment 140, there is a multi-layered transistor 142. The transistor 142 may be contained within a container 144 having walls transparent to the preselected wave lengths associated with the practice of the present invention. Within the container 144 there is also provided a buffer gas generally indicated 146 which, for example, may be argon, helium, or other noble gas, and may be at any desired pressure, for example, within the range of one Milli Torr to one thousand atmospheres, as desired. An electric furnace, schematically indicated at 148, may be utilized to heat the transistor 142 for atomization of the sub-surface layer thereof.

A laser 150 which may be similar to the laser 72 described above powered by a power supply 152 which may be similar to the power supply 76 described above generates a photon beam 154 having photons with a wave length corresponding to the resonant transitions selected for the particular atoms in the sub-surface layer 142 that are to be detected.

The detector 156 having a filter 158 which may be similar to the detector 86 and filter 90, respectively, described above is oriented to receive the non-resonant fluorescence 157 from the particular atoms in the subsurface layer to be detected and generates a first information signal 160 having a magnitude proportional thereto. The first information signal 160 is transmitted to the signal processor 162. A beam splitter 164 is provided in the path of the photon beam 154 and transmit a portion thereof to a power meter 155 which may be similar to the power meter 84 described above which generates a second information signal 159 which is transmitted to the signal processor 162. The signal processor 162 ratios the first information signal 160 and second information signal 159 to provide an output signal 160 having a magnitude proportional to the ratio which is displayed in a display means 163 which may be similar to the display means 100 described above. The laser 150 and detector 156 are operatively connected together so that the laser scans the surface area 142' of the transitor 142 in a predetermined path with the detector 156 continually oriented to receive the non-resonant fluorescent signal 157 emitted from the atoms to be detected. If there is an imperfection in the outer most surface coating of the transistor 142 the atomization provided by electric furnace 148 will cause atoms from the subsurface layer to migrate through such an imperfection and these atoms will be detected.

This concludes the description of the preferred embodiments of the present invention. From the above it can be seen that there has been provided a method and apparatus for detecting comparatively low atomic densities and which may be utilized for gaseous atoms at virtually any desired pressure. Those skilled in the art may find many variations and adaptations of the invention described herein and the appended claims are intended to cover all such variations and adaptations falling within the true scope and the spirit thereof.

I claim:

1. An arrangement for detecting predetermined atoms wherein the atoms have a plurality of energy levels and photon inducible transitions between a first and a second energy level thereof at a resonant wave length and non-resonant fluorescent transition between a third and a fourth energy level thereof at a non-resonant wave length different from said resonant wave length, and collision inducible transitions between at least one of the second to third energy level transitions and fourth to first energy level transitions, comprising, in combination:
   a gaseous sample containing said predetermined atoms to be detected;
   photon beam generating means for generating a photon beam having a preselected intensity and said photon beam containing photons at said resonant wave length and substantially free of photons at said non-resonant wave length of said predetermined atoms for irradiating said gaseous sample with said photon beam to induce transitions of a predetermined portion of said atoms from said first to said second energy levels thereof;
   buffer gas means in regions containing said gaseous sample for inducing said at least one collision inducible transitions of said atoms; and
   detection means in energy receiving relationship to said gaseous sample for detecting said non-resonant fluorescent wave length and generating a first information signal having a magnitude proportional to the intensity thereof whereby said intensity of said non-resonant fluorescent wave length is proportional to the atomic density of said predetermined atoms.

2. The arrangement defined in claim 1 wherein:
said preselected intensity of said photon beam is the saturation intensity.

3. The arrangement defined in claim 2 wherein:
said third energy level is different from said second energy level, and said buffer gas means provides collision inducible transitions of said predetermined atoms between said second and said third energy levels.

4. The arrangement defined in claim 3 wherein:
said third energy level is higher than said second energy level.

5. The arrangement defined in claim 3 wherein:
said third energy level is lower than said second energy level.

6. The arrangement defined in claim 2 wherein:
said fourth energy level is different from said first energy level, and said buffer gas means provides collision inducible transitions of said predetermined atoms between said fourth and said first energy levels.

7. The arrangement defined in claim 6 wherein:
said fourth energy level is higher than said first energy level.

8. The arrangement defined in claim 6 wherein:
said fourth energy level is lower than said first energy level.

9. The arrangement defined in claim 3 wherein:
said fourth energy level is the same energy level as said first energy level.

10. The arrangement defined in claim 3 wherein:
said fourth energy level is different from said first energy level, and said buffer gas means provides collision inducible transitions of said predetermined atoms between said fourth and said first energy levels.

11. The arrangement defined in claim 10 wherein:
said third energy level is higher than said second energy level.

12. The arrangement defined in claim 10 wherein:
said third energy level is lower than said second energy level.

13. The arrangement defined in claim 10 wherein:
said fourth energy level is higher than said first energy level.

14. The arrangement defined in claim 10 wherein:
said fourth energy level is lower than said first energy level.

15. The arrangement defined in claim 1 wherein:
said buffer gas means further comprises a noble gas.

16. The arrangement defined in claim 1 wherein:
said buffer gas means further comprises air.

17. The arrangement defined in claim 1 wherein:
said buffer gas means further comprises the gaseous products of combustion of a predetermined combustible fuel mixture.

18. The arrangement defined in claim 2 wherein:
said gaseous sample is maintained at substantially one atmosphere pressure.

19. The arrangement defined in claim 1 and further comprising:
atomizer means for providing said gaseous sample.

20. The arrangement defined in claim 19 wherein:
said atomizer means comprises an electric furnace.

21. The arrangement defined in claim 19 wherein:
said atomizer means comprises a combustion flame atomizer.

22. The arrangement defined in claim 19 wherein:
said atomizer means comprises means for ion beam bombardment.

23. The arrangement defined in claim 19 wherein:
said atomizer means comprises an electric spark discharge.

24. The arrangement defined in claim 19 wherein:
said atomizer means comprises microwave discharge means.

25. The arrangement defined in claim 1 wherein:
said photon beam generator means comprises a laser.

26. The arrangement defined in claim 25 and further comprising:
means for cyclically varying said predetermined intensity of said photon beam.

27. The arrangement defined in claim 26 and further comprising:
power meter means for detecting the intensity of said photon beam and generating a second information signal having a magnitude proportional to said measured intensity;
signal processing means connected to said power meter means for receiving said second information signal and connected to said detection means for receiving said first information signal for generating a third information signal having a magnitude proportional to the ratio of said first and said second information signals.

28. The arrangement defined in claim 26 and further comprising:
means for cyclically varying the intensity of said photon beam;
and said signal processing means further comprises:
means for rejecting an AC component of said first and said second information signals.

29. A method of detecting predetermined atoms wherein the atoms have a plurality of energy levels and photon inducible transitions between a first and a second energy level thereof at a resonant wave length and non-resonant fluorescent transitions between a third and a fourth energy level thereof at a non-resonant wave length different from said resonant wave length, and collision inducible transitions between at least one of the second to third energy level transitions and fourth to first energy level transitions, comprising the method of:
irradiating a gaseous sample containing said predetermined atoms with a photon beam having a preselected intensity and containing photons having said resonant wave length to induce transitions of said atoms between said first and said second energy levels thereof and said photon beam substantially free of photons at said non-resonant wave length;
exposing said gaseous sample to a buffer gas to induce said at least one collision inducible transition of said atoms;
detecting the intensity of the non-resonant fluorescent wave length; and
generating a first information signal having a magnitude proportional to the measured intensity of said detected intensity whereby said intensity of said non-resonant fluorescent wave length is proportional to the atomic density of said predetermined atoms.

30. The method defined in claim 29 wherein:
said preselected intensity is the intensity corresponding to saturation of said predetermined atoms in said gaseous sample.

31. The method defined in claim 29 and further comprising the step of:
cyclically varying the intensity of said photon beam over a predetermined intensity range.

32. The method defined in claim 31 and further comprising the step of:
maintaining said gaseous sample at a pressure corresponding to substantially one atmosphere pressure.

33. The method defined in claim 30 and further comprising the step of:
measuring the intensity of said photon beam;
generating a second information signal having a magnitude proportional to the measured intensity of said photon beam;
comparing the magnitude of said first information signal with said second information signal and generating a third information signal having a magnitude proportional to the ratio therebetween.

* * * * *